(12) United States Patent
Kovacs

(10) Patent No.: US 11,957,628 B2
(45) Date of Patent: Apr. 16, 2024

(54) STRAP CLAMP ASSEMBLY

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 0 days.

(21) Appl. No.: 17/879,649

(22) Filed: Aug. 2, 2022

(65) Prior Publication Data

US 2022/0362084 A1 Nov. 17, 2022

Related U.S. Application Data

(63) Continuation-in-part of application No. 15/186,451, filed on Jun. 18, 2016, now abandoned, which is a
(Continued)

(51) Int. Cl.
*A61G 13/10* (2006.01)
(52) U.S. Cl.
CPC ................................. *A61G 13/101* (2013.01)
(58) Field of Classification Search
CPC .. A61G 13/101; A61G 13/12; A61G 2203/78; A61G 13/1205; A61G 13/121; A61G 13/122; A61G 13/1225; A61G 13/123; A61G 13/1235; A61G 13/124; A61G 13/1245; A61G 13/125; A61G 13/1255; A61F 5/3776; F16B 2/10; F16B 2/065; F16B 2/12; B25B 5/067; B25B 5/082; B25B 5/101; B25B 5/125; B25B 3/00; B25B 5/163; B25B 5/10; Y10T 24/44291; Y10T 403/32606; Y10T 403/591; Y10T 403/593; Y10T 403/32204; F16M 13/022; F16C 11/0604; A61B 2090/571
(Continued)

(56) References Cited

U.S. PATENT DOCUMENTS

| 600,389 A | * | 3/1898 | Swan | ...................... B25B 5/163 |
| | | | | 269/258 |
| 1,403,580 A | * | 1/1922 | Venema | .................. B25B 5/102 |
| | | | | 269/207 |

(Continued)

*Primary Examiner* — Ingrid M Weinhold
(74) *Attorney, Agent, or Firm* — Wasserbauer Law, LLC; Damian G. Wasserbauer, Esq.; Nicholas E. Blanton, Esq.

(57) ABSTRACT

A clamping device configured to secure a strap to a rail of a support table or operating table is provided, which prevents the patient from slipping, provides optimal patient stability when the table is placed in angle positions, and eliminates patient re-positioning during surgical procedure. The clamping device includes a body portion having a plurality of rail arms that form a rail channel, the clamping device including a pivot jaw assembly with jaw rail flange portions coupled to sides of the body portion. The pivot jaw is hingedly operated between an open and closed position. The rail arms further include a strap channel configured to hold a strap disposed around the side rail, and to secure the strap to the rail using a clamp bar via force exerted on rail and jaw flange portions of the clamp assembly, to effectively clamp the strap to the table.

3 Claims, 15 Drawing Sheets

Related U.S. Application Data continuation-in-part of application No. 15/050,290, filed on Feb. 22, 2016, now Pat. No. 11,510,836, and a continuation-in-part of application No. 13/999,289, filed on Jan. 22, 2014, now abandoned.

(58) Field of Classification Search
USPC ... 248/228.4, 231.51, 229.13, 229.23, 228.6, 248/229.15, 229.25, 231.71
See application file for complete search history.

(56) References Cited

U.S. PATENT DOCUMENTS

| | | | | |
|---|---|---|---|---|
| 2,636,528 | A * | 4/1953 | Golnick | B25B 1/125 269/182 |
| 2,649,123 | A * | 8/1953 | Gulland | B25B 5/163 269/261 |
| 2,768,664 | A * | 10/1956 | Morgan | B25B 5/101 81/133 |
| 2,894,548 | A * | 7/1959 | Peck | B25B 5/102 269/902 |
| 3,981,492 | A | 9/1976 | Hallmann et al. | |
| 4,074,899 | A * | 2/1978 | Hochstetler | B25B 5/101 269/902 |
| 4,105,344 | A * | 8/1978 | Rousom | B25B 5/102 403/77 |
| 4,213,589 | A | 7/1980 | Pierron et al. | |
| 4,355,631 | A | 10/1982 | LeVahn | |
| 4,653,482 | A | 3/1987 | Kurland | |
| 4,707,770 | A * | 11/1987 | Van Duyn | B60Q 1/0683 403/77 |
| 4,901,964 | A | 2/1990 | McConnell | |
| 5,152,486 | A | 10/1992 | Kabanek et al. | |
| 5,362,021 | A | 11/1994 | Phillips | |
| 5,400,772 | A | 3/1995 | LeVahn et al. | |
| 5,427,364 | A * | 6/1995 | Zborschil | B25B 5/16 269/166 |
| 5,433,222 | A | 7/1995 | Boomgaarden | |
| 5,701,991 | A | 12/1997 | Helmetsie | |
| 5,741,210 | A | 4/1998 | Dobrovolny | |
| 6,431,534 | B1 * | 8/2002 | Orosz | B25B 5/163 269/268 |
| 6,564,406 | B2 | 5/2003 | VanSteenburg | |
| 6,622,324 | B2 | 9/2003 | VanSteenburg | |
| 6,622,980 | B2 | 9/2003 | Boucher | |
| 7,520,007 | B2 | 4/2009 | Skripps | |
| 7,624,958 | B2 | 12/2009 | Ropertz et al. | |
| 7,962,982 | B1 | 6/2011 | Fellrath | |
| 8,051,515 | B1 | 11/2011 | Kring | |
| 8,313,095 | B2 * | 11/2012 | Kloepfer | B25B 5/163 269/166 |
| 8,464,720 | B1 | 6/2013 | Pigazzi et al. | |
| 8,511,314 | B2 | 8/2013 | Pigazzi et al. | |
| 8,539,621 | B2 | 9/2013 | West | |
| 8,985,566 | B2 * | 3/2015 | Chuang | B25B 5/102 269/6 |
| 9,022,334 | B1 | 5/2015 | DeMayo | |
| 9,308,626 | B2 * | 4/2016 | Chuang | B25B 5/102 |
| 9,463,554 | B2 * | 10/2016 | Blake, III | B25B 5/163 |
| 11,248,634 | B2 * | 2/2022 | Shetty | F16B 2/10 |
| 2001/0039680 | A1 | 11/2001 | Boucher et al. | |
| 2002/0061225 | A1 | 5/2002 | Boucher | |
| 2003/0102614 | A1 | 6/2003 | Foshag et al. | |
| 2006/0255220 | A1 | 11/2006 | Skripps | |
| 2010/0275377 | A1 | 11/2010 | West | |
| 2012/0126079 | A1 | 5/2012 | Russell | |
| 2013/0019883 | A1 | 1/2013 | Worm et al. | |
| 2014/0165340 | A1 * | 6/2014 | Chuang | B25B 5/102 24/486 |
| 2016/0023330 | A1 * | 1/2016 | Chuang | B25B 5/102 269/246 |

* cited by examiner

STRAP CLAMP ASSEMBLY

CROSS-REFERENCE TO RELATED APPLICATIONS

This application is a continuation-in-part and claims the benefit of co-pending U.S. patent application Ser. No. 15/186,451, filed Jun. 18, 2016, entitled "Strap Clamp Assembly", which is a continuation-in-part and claims the benefit of U.S. patent application Ser. No. 13/999,289, filed Jan. 22, 2014, entitled "Operating table patient support pad clamp", and also is a continuation and claims the benefit of U.S. patent application Ser. No. 15/050,290, filed Feb. 22, 2016, entitled "Pad Assembly, System, Method Of Pre-Load Positioning Of Patient For Medical Procedure And Kit", which are incorporated by reference in their entirety.

FIELD OF THE INVENTION

The present invention relates to patient positioning systems for use in surgical procedures and, more particularly, to a clamping device that secures a strap to a rail of a support and/or operating table thereby preventing the patient from slipping, providing optimal patient stability when the operating table is placed in angled positions, and eliminating patient re-positioning during surgical procedure.

BACKGROUND OF THE INVENTION

In the prior art, many of the positioning devices use straps secured to the side rails of the operating table to prevent the patient from slipping during surgical procedures. In some instances the straps are attached to a patient positioning pad that may be formed of various materials, e.g., foam, high density open cell foam materials, gel, beanbag, shoulder restraints, braces, and tape. Some of the shortcomings of these prior art positioning devices are that they do not meet patient positioning demands of new advanced robotic surgical procedures that require holding a patient in a desired position in any angle for a desired surgical procedure, e.g., front-to-back, back-to-front, or side-to-side. Moreover, these prior art positioning devices may allow the patient to slip when placed in steep Trendelenburg positions that requires re-positioning during surgical procedures, e.g., patient slippage occurs with heavier and larger sized patients are placed in steep Trendelenburg positions.

Patient slippage on the operating table is frequently encountered when steep angles are employed due to gravity, reduced friction, and/or fluids generated or involved in a surgical procedure. Modern robotic surgical procedures, for example, position the operating room table in various angles (e.g., Trendelenburg, reverse-Trendelenburg or otherwise side-to-side angles) to move organs away from the site of the surgical procedure and may use a patient positioning pad system. Even with a patient positioning pad system, the slippage problem still occurs in surgical procedures, such as with larger, heavier patients positioned on an operating table that is oriented to have the patient's head-elevated, to have the patient's feet-elevated, and/or to elevate from side-to-side. It is undesirable for the patient to slip, shift or otherwise move on the operating table during the surgical procedure especially with an increase in modern, endoscopic surgical procedures using robotic tools, as this may cause tissue and nerve damage as well as delays due to re-positioning. In robotic assisted surgical procedures, slipping and shifting of the patient on the operating table causes movement of the site of the surgical procedure. Numerous problems are caused when the site of the surgical procedure shifts including, for example, trauma, tearing at the site, or other tissue and nerve injuries to the patient that may cause adverse events and prolong the recovery of the patient. As a result, there is a long-felt need to eliminate the patient from shifting or otherwise changing position on the operating table during a surgical procedure.

Some of the shortcomings of the prior art clamping devices are that conventional rail clamps are not useful to secure operating table straps or the straps of a patient positioning pad system as the straps prevent a rail clamp from joining and/or sliding along the rail. Patient positioning pad systems rely on looping straps around the side rail of the operating table so as to attach positioning pad to the operating table. Some practices place additional operating table straps over the chest and limbs of the patient, whereby these prior art methods can cause unnecessary pressure on the neck, shoulders or arms, resulting in, for example, nerve damage and pressure ulcers. As a result, a need exists for a clamping device for an operating table configured to join a strap to the rail of the operating table at any point between the ends of the rail.

Some of the shortcomings of conventional rail clamping devices include requiring placement at an exact location to attach to a side rail of the operating table. Conventional rail clamps are designed to join at a rail post by positioning the rail clamp slot adjacent the rail post, allowing clearance over the rail, or by sliding from an end of the rail to the desired location. Conventional rail clamps are prevented from joining at the rail post when straps are used because (1) the strap secured around the rail prevents positioning the rail clamp slot adjacent the rail post, and (2) the strap prevents the sliding downward and rotational movement necessary to attach the rail to the operating table. As a result, conventional rail clamps are prevented from joining the rail at any point between the ends of the rail. Therefore, a need also exists for a clamping device configured to join at any point between the ends of the rail when using straps and or straps of a patient positioning pad system.

SUMMARY OF THE INVENTION

It is an object of the present invention to provide a rail clamp assembly to secure the straps of a patient positioning pad firmly to the side rail of an operating table during a surgical procedure so as to eliminate the patient from shifting on the operating table, or otherwise changing position, on the patient positioning pad.

It is an object of the present invention to provide a rail clamp assembly to join firmly to the side rail of an operating table at any point along the side rail during a surgical procedure, when patient positioning pads are used.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIGS. 3A, 3B and 3C illustrate rail clamps of the prior art wherein FIG. 3A is a schematic perspective view illustrating a rail clamp of the prior art, FIG. 3B is a schematic, bottom view illustrating the arm and body of a rail clamp of the prior art, and FIG. 3C is an expanded perspective view illustrating a rail clamp positioned adjacent a positioning system strap with the connecting to the side rail over a rail post of the prior art;

DESCRIPTION OF THE EMBODIMENTS

Figure 1:
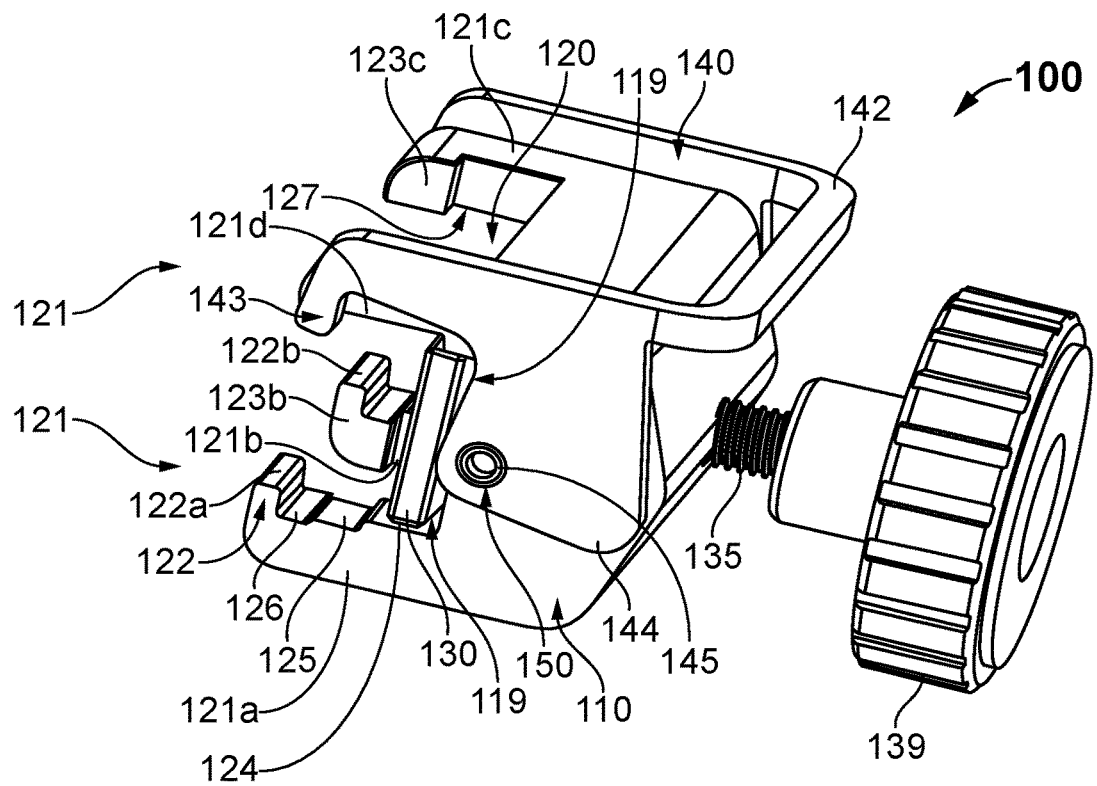
FIG. 1 is a schematic, bottom perspective view of a clamp assembly in accordance with an embodiment of the present invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As is illustrated in FIGS. 1-2, and 4-23D, the present invention relates to a clamp assembly 100 for securing to a rail 102 of a support table and/or operating table 104, sometimes called an OR table, as is illustrated in FIGS. 8A-8B, 10-13, and 17. According to one or more embodiments of the present invention, the clamp assembly 100 is described in the environment of a surgical procedure where the operating table 104 is angled with the patient secured by a strap 106 to the rail 102 of the operating table 104. Similarly, the clamp assembly 100 can clamp to one or more straps 106 of a patient positioning pad system 108 and such patient positioning pad systems 108 are generally available in the marketplace, for example, from Innovative Medical Products, Inc. of Plainville, Connecticut sold under the product name TrenMax™ and Xodus Medical Inc. Pittsburgh, PA as shown U.S. Pat. Nos. 8,464,720 and 8,511,314. It should be appreciated by one skilled in the art that the clamp assembly 100 may be useful for clamping individual straps 106, items and things to a rail 102 of the support and/or operating table 104. According to the advantages of the present invention, the clamp assembly 100 clamping a strap 106 to the rail avoids slippage problems of conventional straps and/or patient positioning pad systems so as to reduce trauma that may be caused by slippage to patients positioned at any angle on the operating table 104 during a surgical procedure including Trendelenburg, reverse-Trendelenburg, and at side-to-side angles.

Figure 3A:
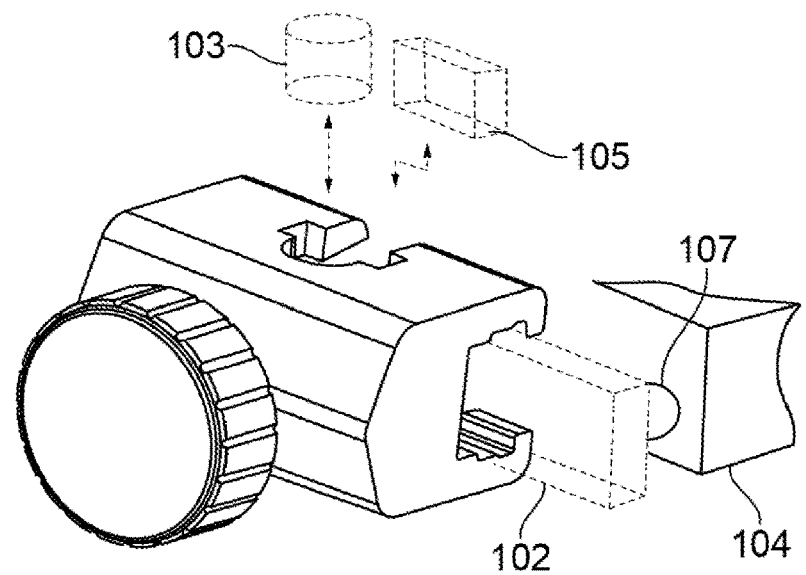
Figure 3B:
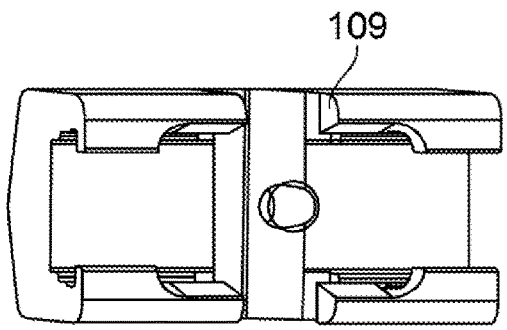
Figure 3C:
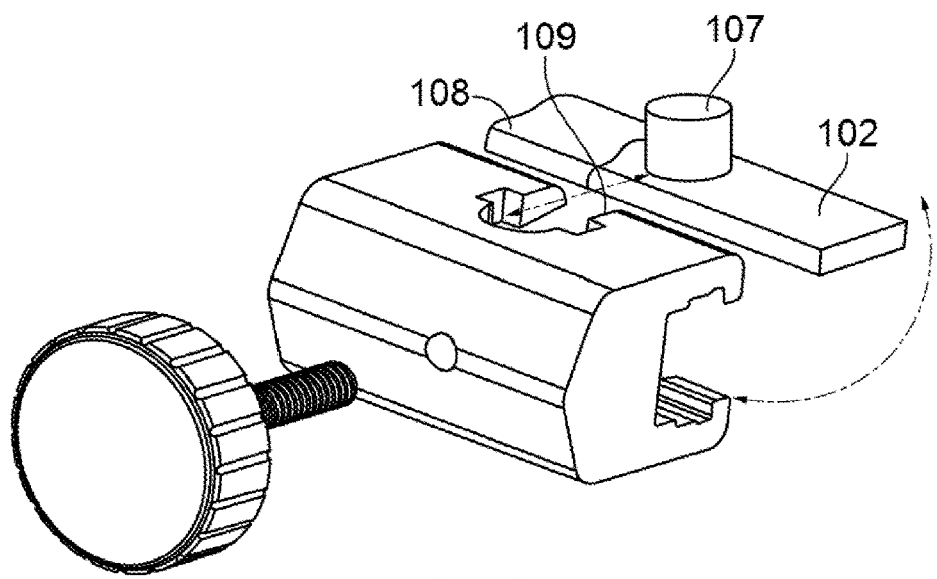
Figure 4:
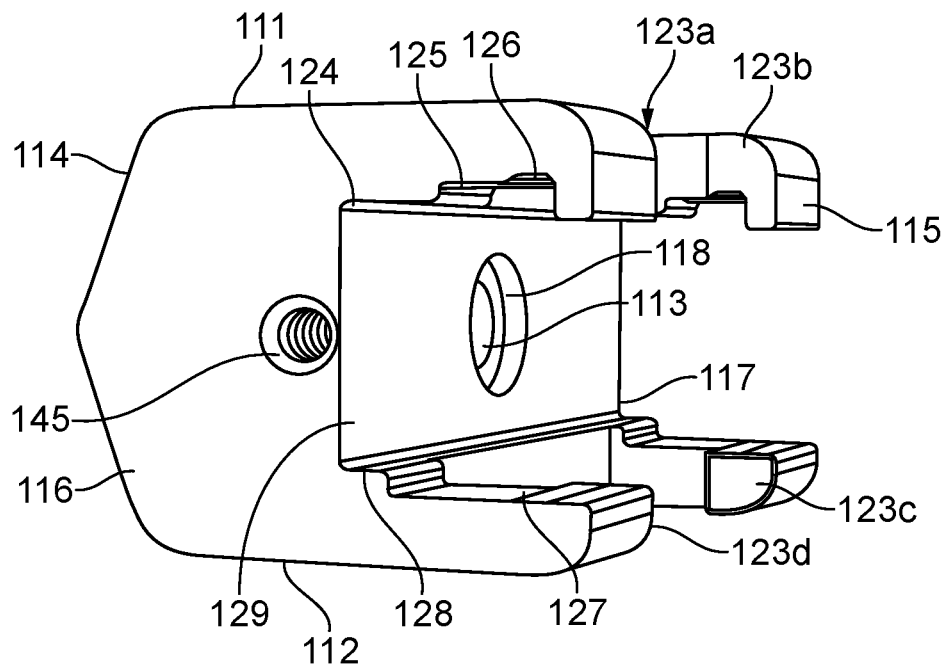
FIG. 4 is a perspective side view illustrating the body of a clamp assembly in accordance with an embodiment of the present invention.
Figure 5:
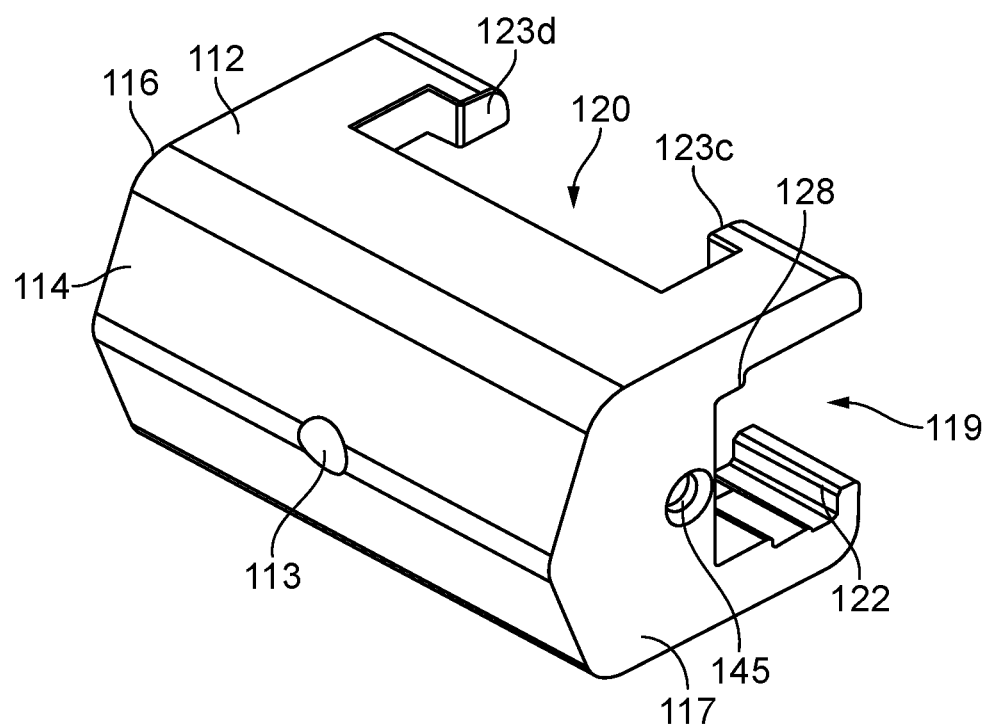
FIG. 5 is a perspective bottom view illustrating the body of a clamp assembly according to the invention.

According to the present invention, as illustrated in FIGS. 3A-3C, prior art rail clamps for retractors and other items and objects are unable to be used to secure straps 106 to the side rail 102 of the operating table 104. Conventional rail clamping devices are used during surgical procedures that are typically secured to a side rail 102 attached at a rail post 107 to the side of the operating table 104. These prior art rail clamping devices utilize a construction with a clamp member and a set screw, whereby the set screw engages the side rail which secures the clamping member to the side rail 102, whereby a round post 103 or a square post 105 of a surgical attachment, e.g., retractor, limb holder, post or other item is secured thereto, as is shown in FIG. 3A. The set screw and knob of conventional rail clamps is adapted to tighten through a central hole, as is shown in FIG. 3B, allowing a knob and a threaded post to tighten against the round post 103, or square post 105, to the rail 102, or, alternatively, the set screw also may tighten directly to the rail 102. As is illustrated in FIG. 3C, conventional rail clamps can only be joined between the ends of the rail 102 at a rail post 107, whereby a rail clamp slot 109 is positioning adjacent the rail post 107 attaching the rail 102 to the operating table 104 with a sliding downward movement and then rotating the clamp body 90 degrees (90°). A strap 106 of a patient positioning system 108 prevents conventional rail clamping devices from joining at the rail post 107 as well as at any point between the ends of the rail because (1) a strap of the patent positioning pad secured around the rail prevents positioning the rail clamp slot adjacent the rail post, and (2) the strap prevents the sliding downward and rotational movement necessary to attach the rail to the operating table as shown in FIG. 3C. A long-felt need exists for a clamping device to overcome the advantages and a clamping device 100 configured to join at any point between the ends of the rail 102 when using straps 106 and or straps of a patient positioning pad system 108.

As is illustrated in FIGS. 1-2, and 4-12, according to one or more embodiments of the present invention a clamp assembly 100 comprises a body portion 110 configured with a rail channel 119 and a strap channel 120, a clamp bar 130 operably coupled to a swivel screw 135 and knob 139, and a pivot jaw assembly 140. The rail channel 119 and strap channel 120 may be formed to provide a plurality of arms 121 extending from the body portion 110 such as, for example, individually identified upper rail arms 121a, 121b, and lower rail arms 121c, 121d extending from the corners of the body portion 110. Upper rail arms 121a and 121b are utilized as upper rail arm members configured to rest the clamp assembly 100 on the upper surface 102a or top of rail 102. The upper rail arms 121a and 121b may be configured with a rail flange 122, individually identified as rail flanges 122a and 122b, configured to hang the clamp 100 on the rail 102 of the support table 104. Lower rail arms 121c and 121d are utilized as lower arm members configured to slide over on the lower surface 102b or bottom of rail 102 and joining the clamp assembly 100 to the rail 102 is provided by a jaw rail flange portion 143, identified as portions 143a and 143b in FIGS. 1-2, 6, 8A-8B, and 9, of the pivot jaw assembly 140. In addition, the arms 121a, 121b, 121c, and 121d may further be configured with strap flange 123 that extends inwardly from the arms 121a-121d of the body portion 110 such as, for example, individually identified strap flanges 123a, 123b, 123c, and 123d. The body portion 110 may be formed from suitable materials of sufficient strength and durability such as, for example, extruded metal, stainless steel, 6061 T6 aluminum stock, carbon fiber, or other suitable stock materials. The body portion 110 may be milled using computer numeric controlled manufacturing techniques to form arms 121a, 121b, 121c, and 121d. Similarly, CNC manufacturing may be used to form rail flange 122a and 122b, and strap flanges 123a, 123b, 123c, and 123d.

Figure 7:
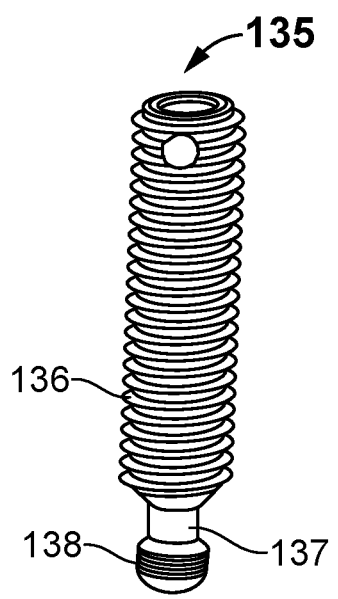
FIG. 7 is a side view illustrating a threaded swivel screw of a clamp assembly in accordance with an embodiment of the present invention.
Figure 8A:
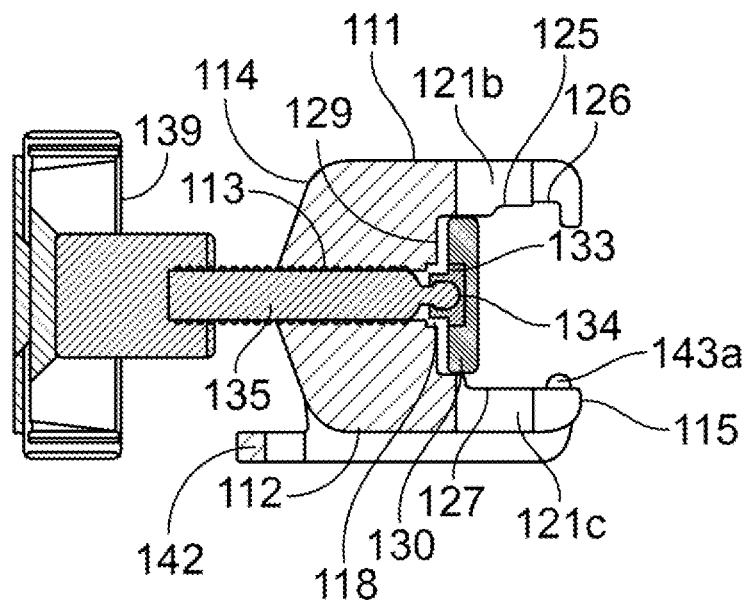
FIGS. 8A and 8B are a cross-sectional, side view, taken along line A-A of FIG. 2, illustrating a clamp assembly clamping a strap to the side rail of an operating table in accordance with an embodiment of the present invention.

As illustrated in FIGS. 1, 2, 4, 5, and 8A-12, the body portion 110 is configured with a top portion 111, a bottom portion 112, a front portion 114, a rear portion 115, side portion 116, and side portion 117. The body portion 110 may be configured with a centrally disposed hole 113 connecting the front portion 114 and rear portion 115 and adapted to accept a swivel screw 135 shown in FIG. 7. Centrally disposed hole 113 also may be configured with a countersink hole 118 adapted to receive a swivel foot 133 of the clamp bar 130 as is shown in FIG. 8A-8B. The body portion 110 may be configured with a rail channel 119 formed in the rear portion 115 and extending between the side portions 116, 117. A strap channel 120 may be formed in the rear portion 115 of the body portion 110 extending between the top and bottom portions 111, 112.

Figure 6:
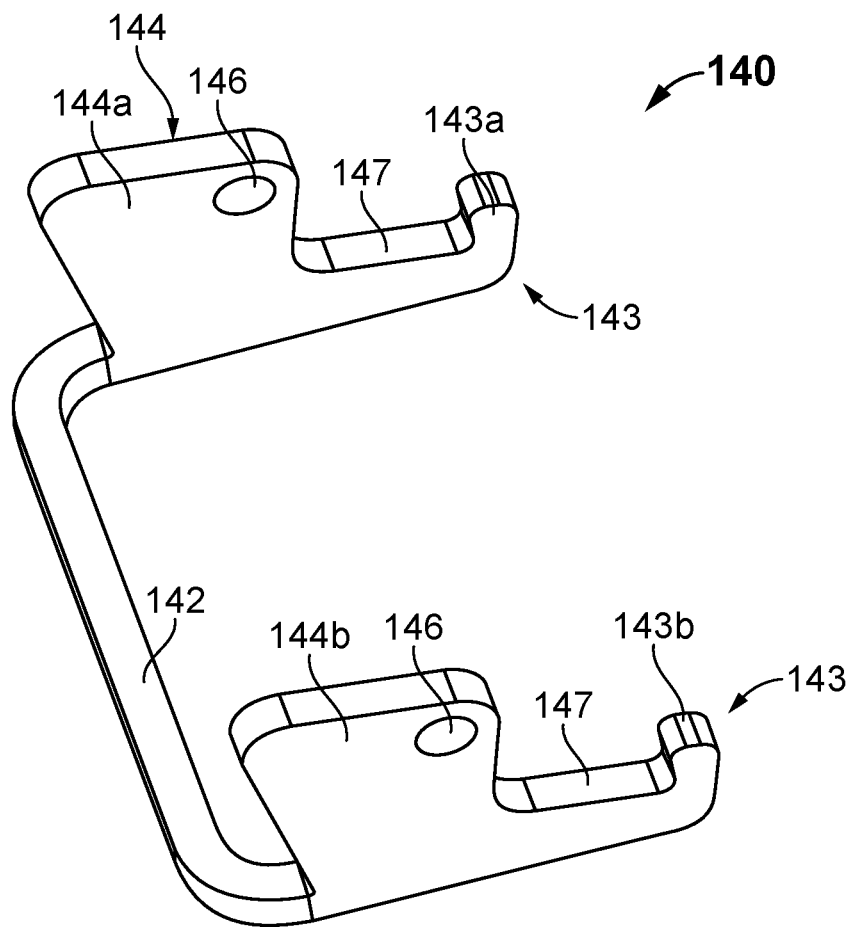
FIG. 6 is a perspective top view illustrating a lever of a clamp assembly in accordance with an embodiment of the present invention.
Figure 8B:
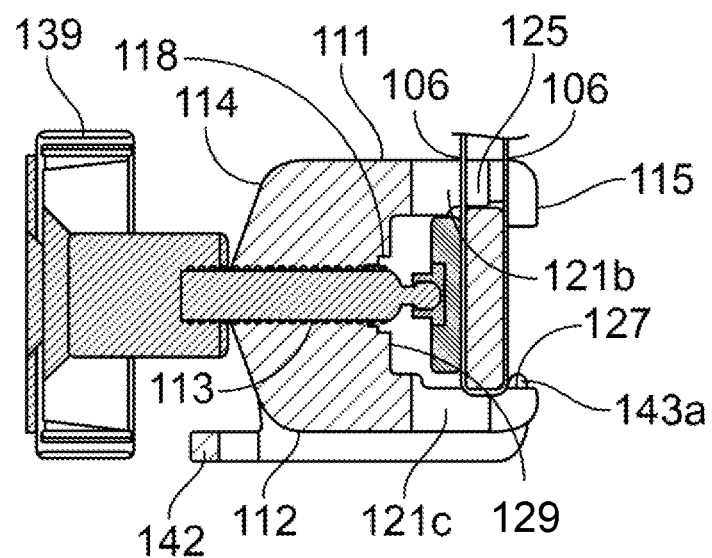

Referring to FIG. 6, a pivot jaw assembly 140 is configured to connect to the base portion 110 so as to provide attachment to the lower part of the rail 102 of the operating table 104. The pivot jaw assembly 140 comprises a jaw of a predetermined shape so as to locate jaw flange portions 143a and 143b in a position to engage a lower surface 102b of the rail 102. The predetermined shape may be elongated, stamped and bent into a U- or C-shape, and positioned adjacent a hold or opening 145 in each side portion 116, 117 of the base portion 110 for operably connecting by a set screw 150 joining the pivot jaw assembly 140 and the body portion 110. The pivot jaw assembly 140 may be formed from suitable materials of sufficient strength and durability such as, for example, extruded metal, stainless steel, 6061 T6 aluminum stock or other suitable stock materials. The predetermined shape of the pivot jaw assembly 140 comprises a handle portion 142, a jaw rail flange portion 143, individually identified jaw rail flange portions 143a and 143b, and a hinge portion 144 configured with holes or openings 146 for attaching the pivot jaw assembly 140 to the body portion 110. The jaw body portion comprises a jaw rail surface 147 for registering on the lower surface 102b of the rail 102 cooperating with jaw rail flange portions 143a and 143b when tightening the clamp assembly 100 as shown in FIGS. 6, 8A-8B and 9. Specifically, the pivot jaw assembly 140 is joined by two set screws 150 via set screw holes 145 formed in each side portion 116, 117 of the hinge portion 144 by these set screws 150 that operably connect the holes or openings 146 in each of the hinge portions 144a and 144b. The jaw rail flange portion 143 operates to engage the rail 102 in a closed position, whereby, individually identified jaw rail flange portions 143a and 143b cooperate with rail flanged portions 122a and 122b when the knob is tightened or loosened moving the clamp bar 130 so as to clamp the strap 106 against rail 102 and urging the jaw rail flange portions 143a and 143b against the rail 102 as illustrated in FIGS. 8A-8B through 12.

Figure 2:
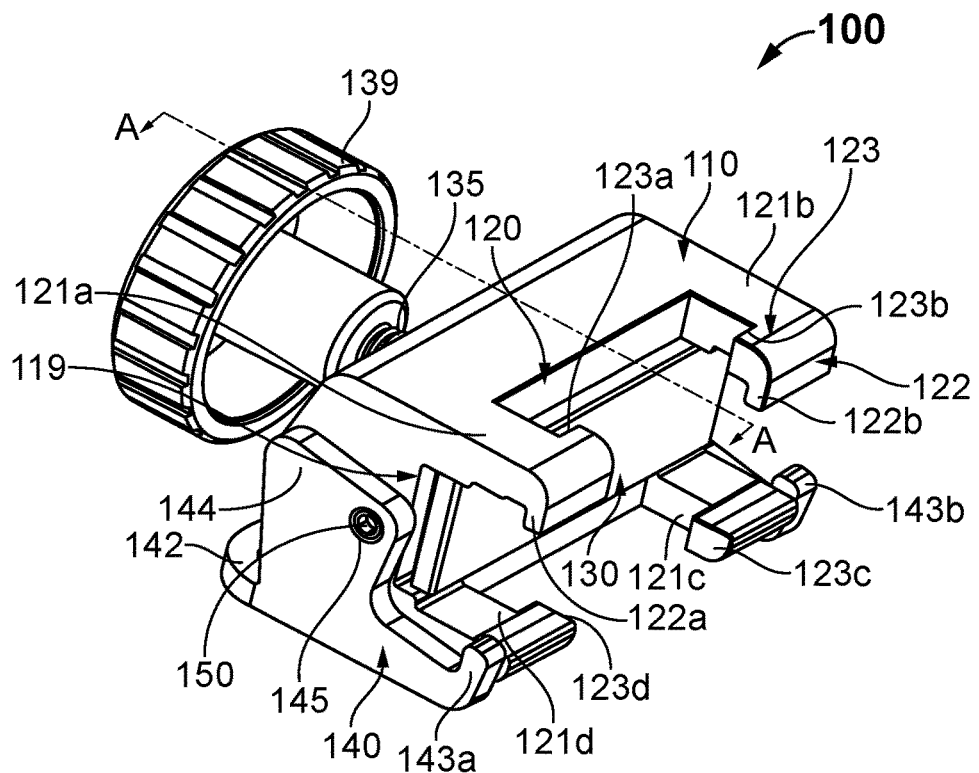
FIG. 2 is a schematic, perspective top view of a clamp assembly in accordance with an embodiment of the present invention.
Figure 10:
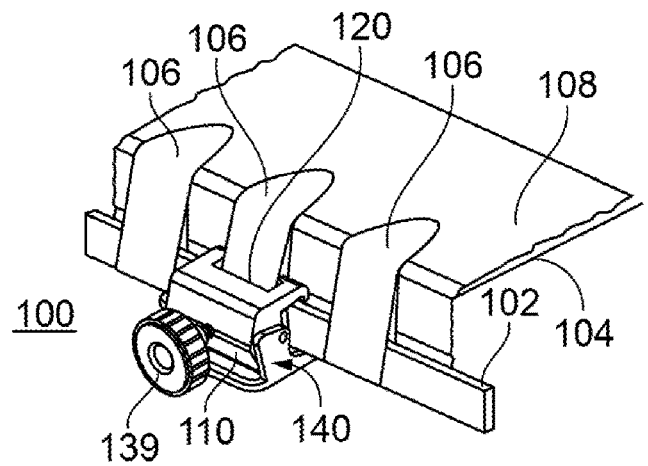
FIG. 10 is a schematic perspective view of a clamp assembly clamping a strap to the side rail of an operating table in accordance with an embodiment of the present invention.
Figure 11:
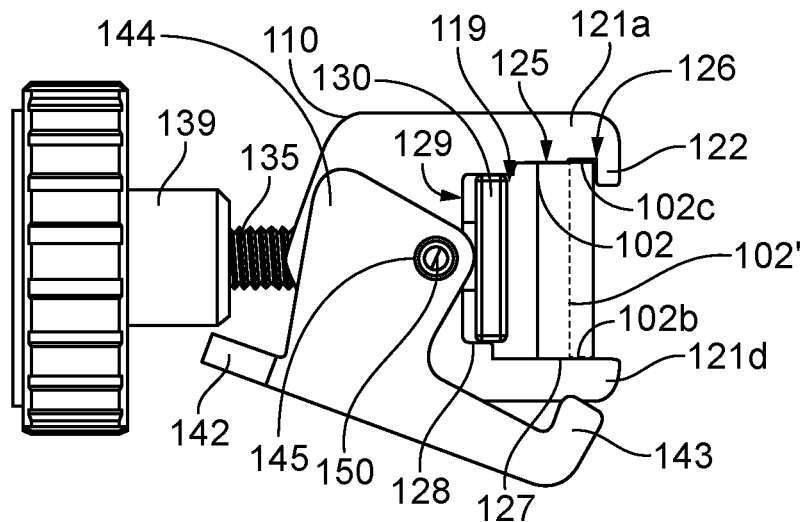
FIG. 11 is a side, perspective view of the clamp in the environment of operably connecting a clamp assembly and pivot jaw assembly in the open position to a side rail of an operating table in accordance with an embodiment of the present invention.
Figure 12:
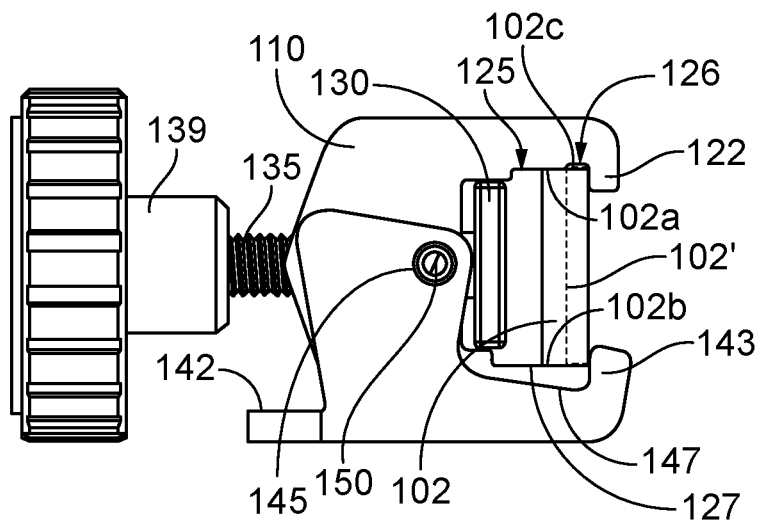
FIG. 12 is a side, perspective view of the clamp in the environment of operably connecting a clamp assembly and pivot jaw assembly in the closed position to a side rail of an operating table in accordance with an embodiment of the present invention.
Figure 13:
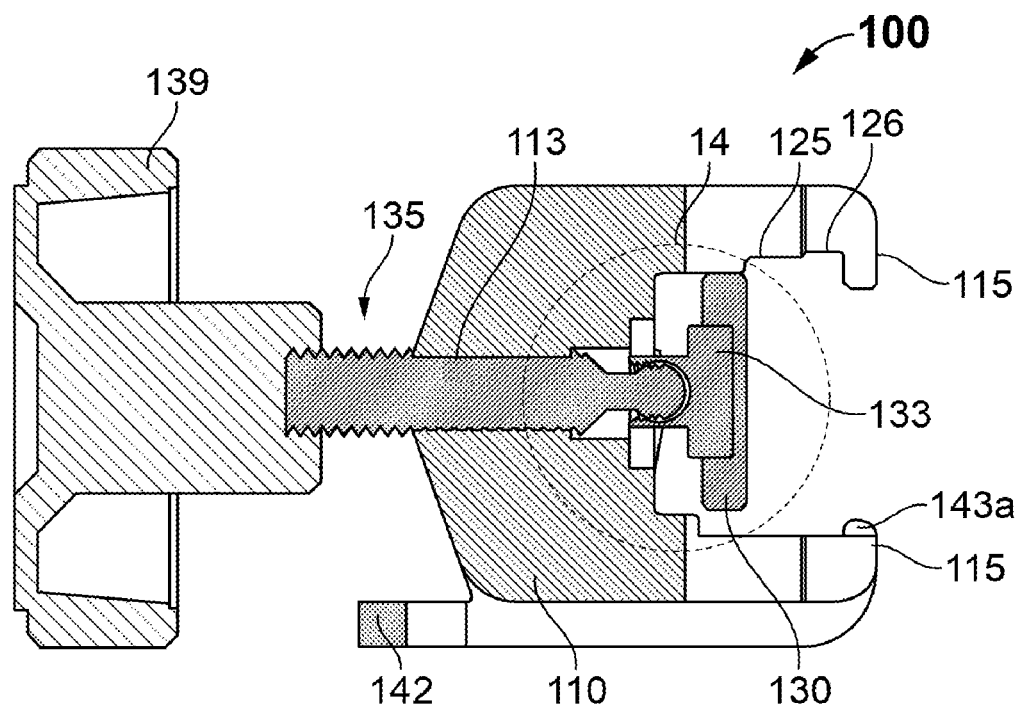
FIG. 13 is a cross-sectional, side view, taken along line A-A of FIG. 2, illustrating a clamp assembly including a swivel foot and swivel screw in accordance with an embodiment of the invention.
Figure 14:
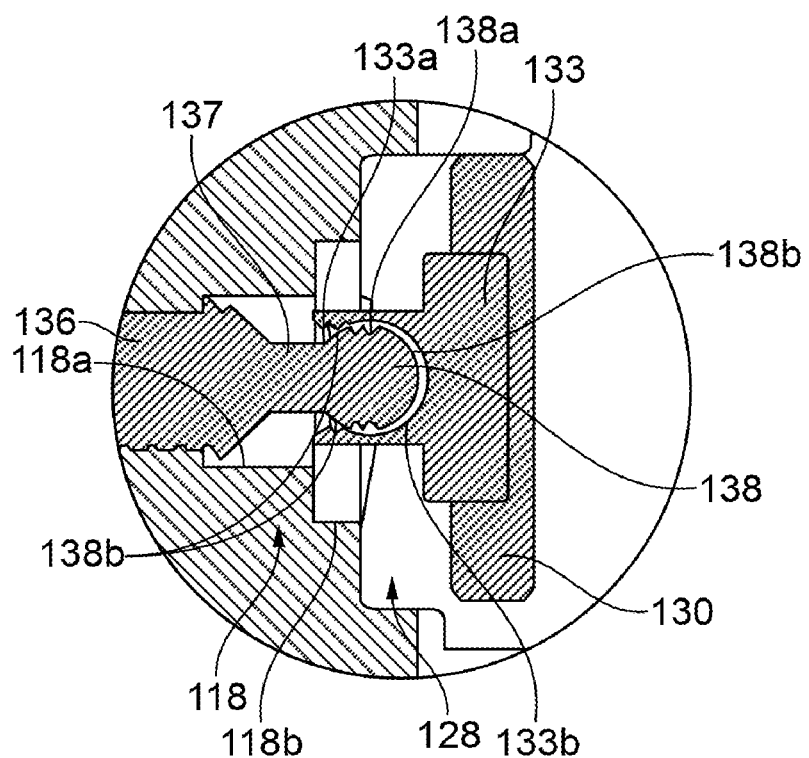
FIG. 14 is an enlarged view in accordance with the line shown in FIG. 13, illustrating a swivel foot and swivel screw of the invention thereof.
Figure 15A:
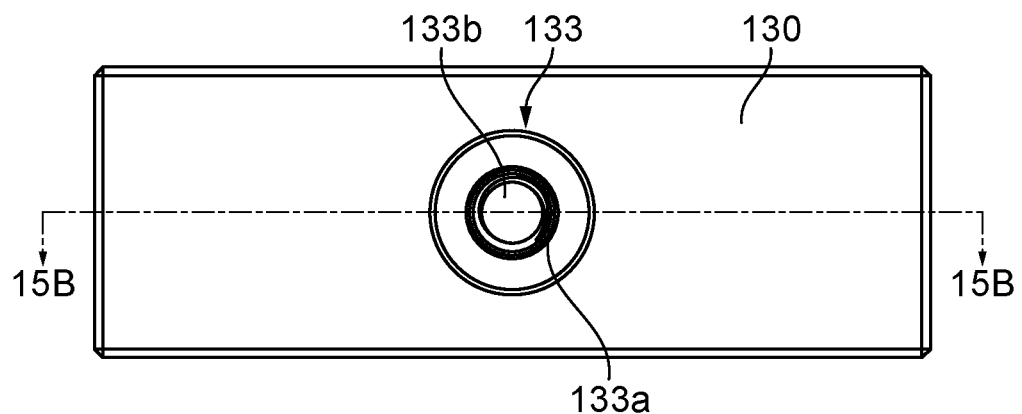
FIG. 15A is a front view of a clamp bar and swivel foot thereof.
Figure 15B:
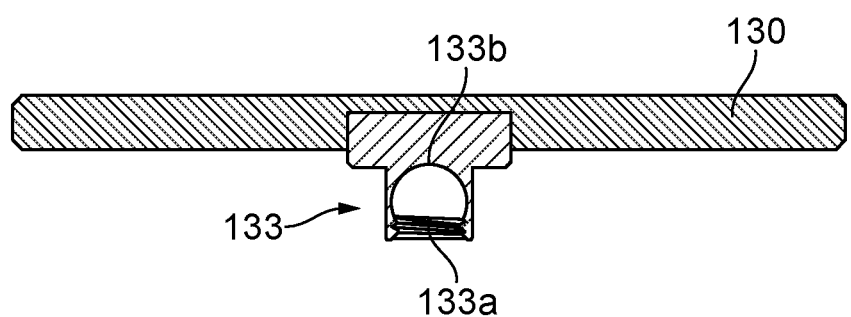
FIG. 15B is a cross-sectional, top view, taken along the line shown in FIG. 15A, illustrating a clamp bar and swivel foot thereof.

Referring to FIGS. 1, 2, 4, 5, 8A-8B, 10-12, the rail channel 119 is dimensioned to accept various dimensions of a side rail of the operating table 104, for example, a rail 102 of a standard dimension shown in FIGS. 8B and 10-12, and a taller, thinner rail 102' of other standard rail dimensions identified by broken-line that registers in the upper surface 102c and surface 126 shown in FIGS. 10, 11 and 12. The rail channel 119 is further configured with a cavity 128 for receiving the clamp bar 130 in the retracted or untightened position, for example, as shown in FIGS. 1 and 2. The cavity 128 is configured with cavity surface 129 that may be formed with the counter sink hole 118 configured to receive the swivel foot 133 so as to allow the clamp bar 130 to retract fully adjacent the cavity surface 129 when attached to the swivel-screw 135.

Figure 9:
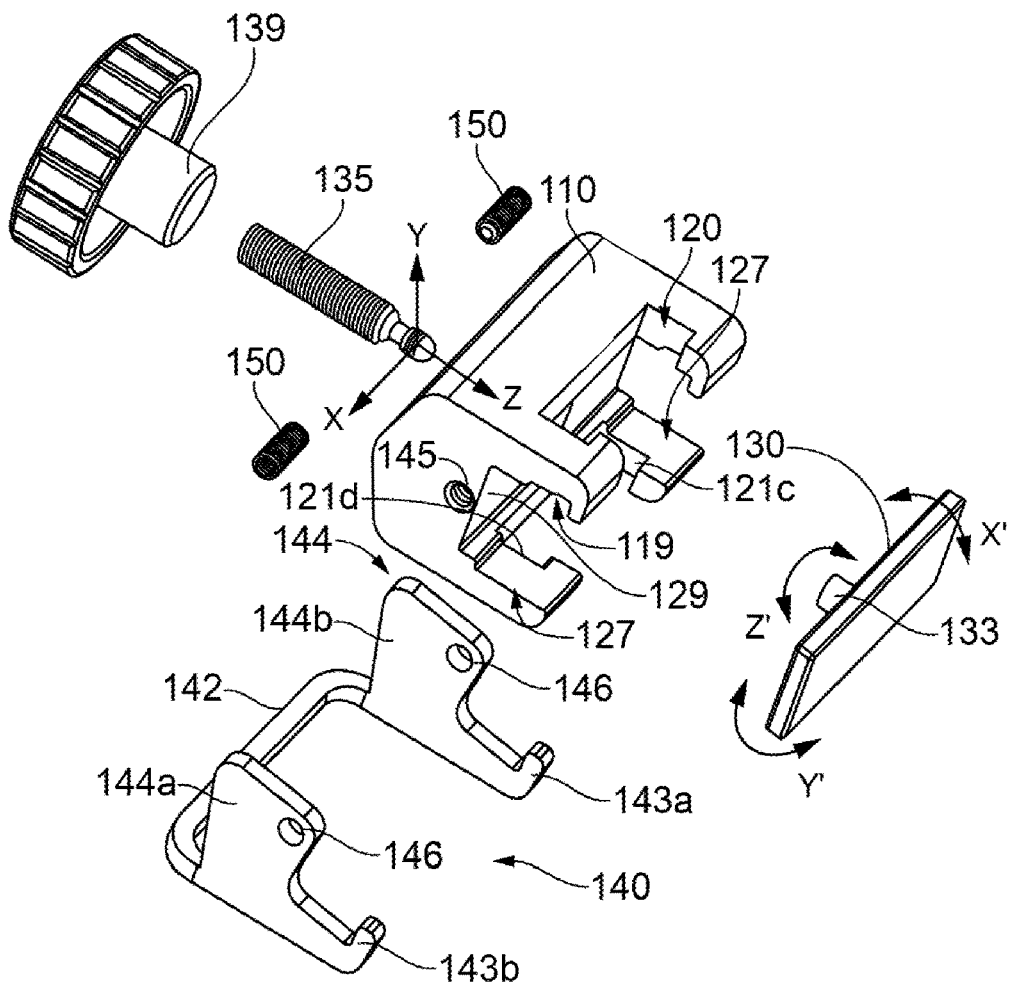
FIG. 9 is a schematic perspective expanded top view of a clamp assembly in accordance with an embodiment of the present invention.

The rail channel 119 may be configured with an upper rail arm surface 124 on upper rail arms 121a, 121b so as to rest on an edge of upper surface 102a of the rail 102 as shown in FIGS. 8A-8B and 10-12. The upper surface 124 may be further formed with a first step 125 and a second step 126 to accommodate different rail 102, 102' dimensions and to improve positioning of the clamp 100 on the upper surface of the rail 102 of the support table 104. For example, the first step surface 125 is useful for registering, aligning the edge of upper surface 102a of the rail 102 so as to abut in adjacent relationship the upper rail arm surface 124 of upper rail arm 121a when tightening the clamp assembly 100 as shown in FIG. 1. The second step surface 126 is useful for registering an edge of upper surface 102a of the rail 102 and/or an edge of upper surface 102c for a thinner dimensioned rail 102' as well as to provide additional space when rotating and fitting the lower arms 121c, 121d over the edge of lower surface 102b of the rail 102. A lower rail arm surface 127 is dimensioned to slide over the edge of the lower surface 102b of the rail 102 and formed to abut adjacent the edge of lower surface 102b when tightening the clamp assembly 100 as shown in FIGS. 8B and 9.

As is illustrated in FIG. 7, the swivel screw 135 is configured with an upper screw portion 136, a transition portion 137, and a lower portion 138. The upper screw portion 136 may be formed with threads adapted to be received in the centrally disposed hole 113 of the body portion 110. The upper screw portion 136 may further be adapted to be received by the knob 139 and secured to the knob 139 by a post or set screw. The swivel screw 135 may be formed from suitable materials of sufficient strength and durability that may be tooled and threaded such as, for example, extruded metal, stainless steel, 6061 T6 aluminum stock or other suitable stock materials.

Referring to FIGS. 7-9, and 13-23D, according to one or more embodiments, a swivel foot 133 is configured to operably connect to the swivel screw 135 so as to provide the clamping action of the clamp bar 130 against the strap 106 against a rail 102 of the operating table 104 and is illustrated in FIGS. 8A-8B. The clamp bar 130 and swivel foot 133 may be formed from suitable materials of sufficient strength and durability such as, for example, extruded metal, stainless steel, 6061 T6 aluminum stock or other suitable stock materials. The lower portion 138 may be formed with threads adapted to be received in the recessed hole 134 of the swivel foot 133, as illustrated in FIGS. 8A-8B. As is illustrated in FIGS. 8A-8B, and 13-14, the swivel foot 133 may be secured to the clamp bar 130 by welding, crimping, or the like. The lower portion 138 may be operably coupled within the recessed hole 134 of the swivel foot 133 to provide wide-ranging clamping of straps 106 of various dimensions to the rail 102. As will be described in further detail below, the swivel screw 135 and clamp bar 130, which may be coupled via a swivel foot 133, allow angular movement of the clamp bar 130 relative to the body portion 110, pivot jaw 140, etc. In this way, the lower portion 138 remains free to rotate within the recessed hole 134 of clamp bar 130, for example, as the swivel screw is advanced through centrally disposed hole 113, so that the clamp assembly 100 can adjust and provide complete clamping of the strap 106 to the rail 102, 102' via movement in three angular directions (e.g., angular rotations X', Y', and Z', taken about X, Y, and Z axes). Therefore, "swivel" in this context may refer to a ball-and-socket type joint. This arrangement advantageously adjusts to provide complete clamping to the straps 106 of various dimensions, thicknesses, and materials as disposed in the rail channel 119.

In operation, as is illustrated in FIGS. 8A-8B and 10-12, the clamp assembly 100 is used to clamp and secure a strap 106 at any point along the rail 102 of an operating table 104. An individual strap 106, as shown in FIG. 8B, and one or more straps 106 of a patient positioning pad 108, as shown in FIG. 10, may be secured around the rail 102 of a support and/or operating table 104. As shown in FIGS. 8B, and 10-12, the clamp assembly 100 may be positioned on the upper surface 102a of the rail 102 with the strap 106 disposed in the strap channel 120 between the arms 121a, 121b, 121c, 121d and the strap flanges 123a, 123b, 123c and 123d. The rail flanges 122a and 122b are position on the rail 102 resting on the upper surface 102a of the rail 102 and the upper rail arm surface 124 (e.g., the first step 125 and the second step 126). The clamp assembly 100 may be rotated slightly towards the rail 102 passing the lower arms adjacent the lower surface 102b of the rail 102, 102' with the pivot jaw assembly 140 opened downwardly as is illustrated in FIG. 11. The pivot jaw assembly 140 may be rotated upwardly to place the jaw rail flange portions 143a and 143b adjacent the rear surface of the rail 102 as is illustrated in FIGS. 8B and 12. The clamp bar 130 of the clamp assembly 100 may be tightened and loosened using knob 139 so as to force the swivel screw 135 to operably connect to the clamp bar 130 to the strap 106 and rail 102, so as to secure the strap 106 to the rail 102 and the clamp assembly 100 to the rail 102. The force of the clamp bar 130 against the strap 106 and rail 102 operably connects the jaw rail flange portions 143a and 143b of the pivot jaw assembly 140 and the rail jaw rail flange portions 122a and 122b of the upper rail arms against the inner surface of the rail 102 so as to secure and hold the strap 106 to the rail 102.

Referring now to FIGS. 13-16C, aspects of the swivel screw 135 and clamp bar 130 according to an embodiment of the present invention are described. The recessed hole 134 as shown in FIG. 8A may be characterized by the arrangement and spacing shown in the cross-sectional view of FIG.

13 (taken along the line A-A of FIG. 2), which illustrates the swivel screw 135 and clamp bar 130 in the context of the clamp assembly 100. As may be seen in the enlarged view of FIG. 14, and in FIGS. 15A and 15B, recessed hole 134 of FIG. 8A, may comprise a left-handed receiver portion 133*a* and swivel foot cavity portion 133*b*. Lower portion 138 of swivel screw 135 may comprise a smooth portion 138*b* forming a substantially spherical profile.

In one embodiment a thread portion provides a connection to the swivel foot cavity portion 133*b*, for example, a portion of the smooth spherical profile may have a left-handed thread portion 138*a*. In an assembled configuration, as in FIG. 14, the lower portion 138 is confined within, and operably coupled to, the swivel foot cavity portion 133*b*, thereby forming a ball-and-socket joint. Accordingly the clamp bar 130 remains free to rotate to accommodate a strap 106 as necessary, owing in part to the slender dimension of the transition portion 137 that allows left-hand thread receiver portion 133*a* to bypass left-hand thread portion 138*a*. Countersink hole 118 may comprise first and second countersink holes 118*a* and 118*b*, which form a complementary shape to that of the swivel foot 133, as shown. As previously mentioned, and as detailed in FIG. 14, first and second countersink holes 118*a* and 118*b* allow clamp bar 130 to remain with cavity 128 when clamp assembly 100 is in a retracted configuration.

Figure 16A:
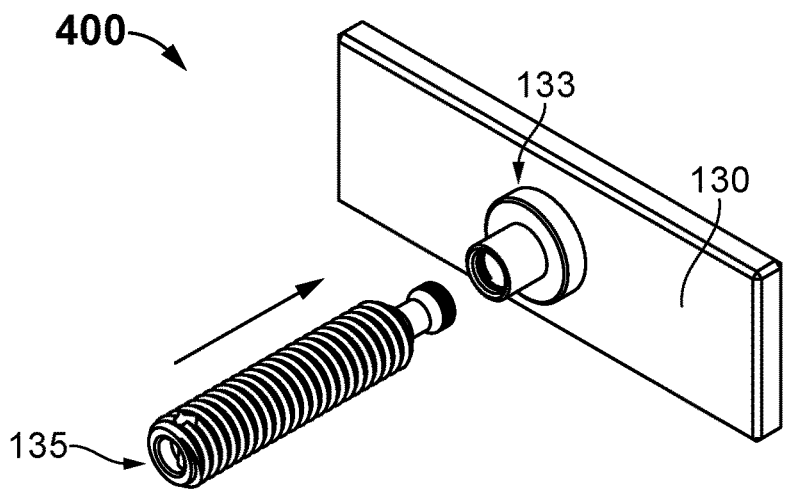
FIGS. 16A-16C illustrate schematic perspective views of a method of assembling a swivel screw and swivel foot in accordance with an embodiment of the invention.
Figure 16B:
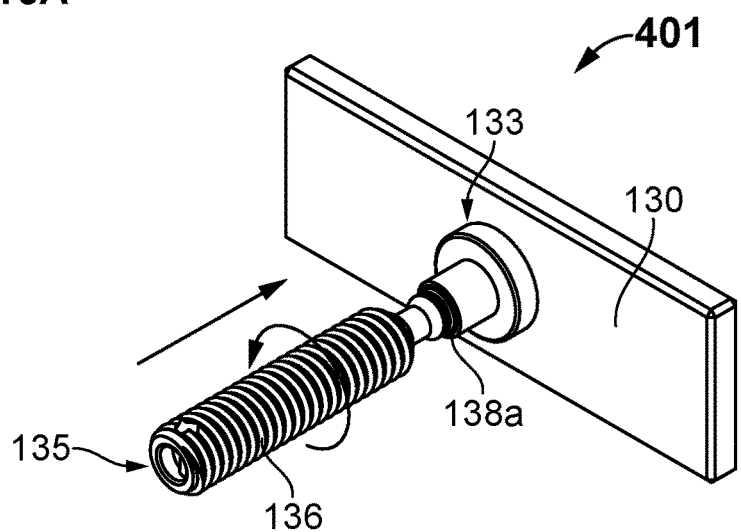
Figure 16C:
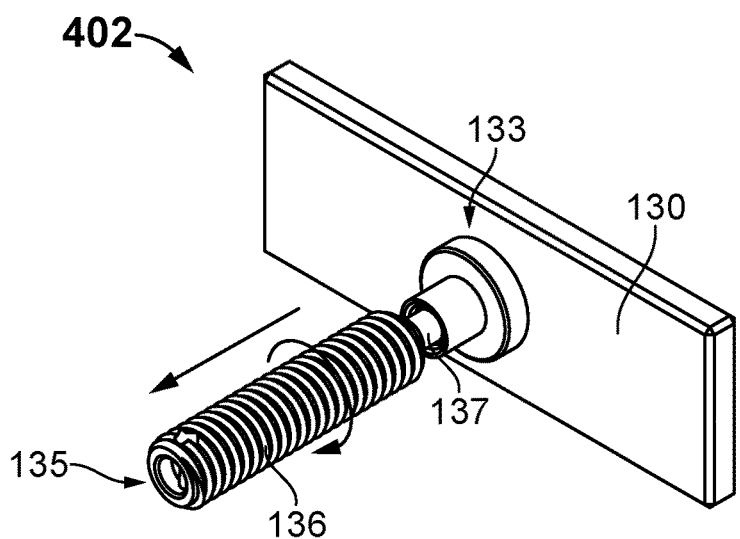
Figure 17:
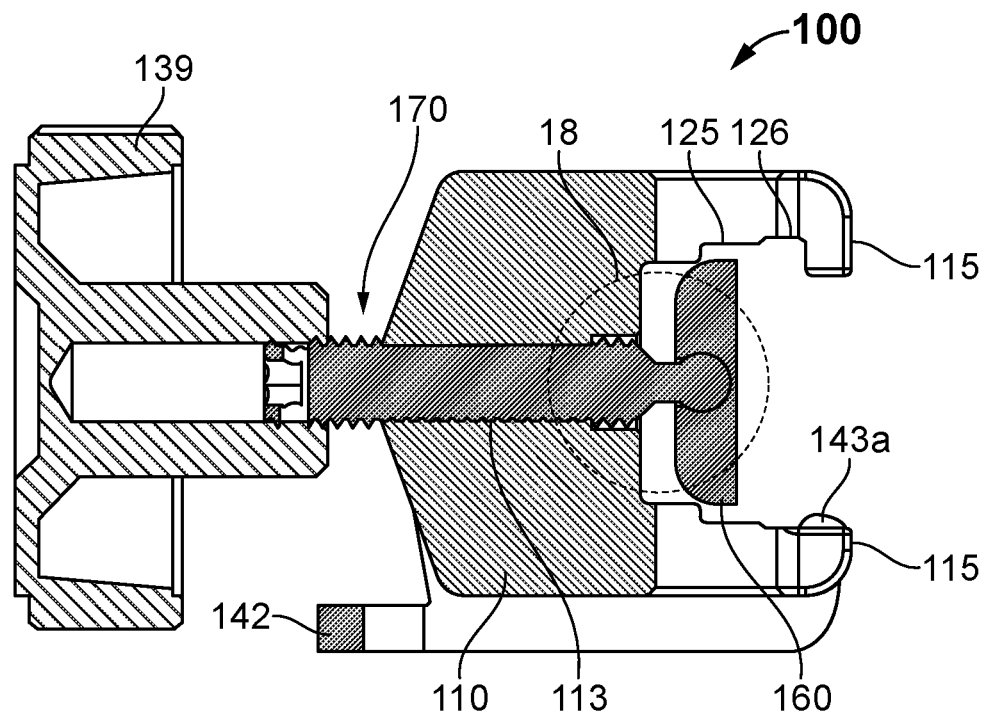
FIG. 17 is a cross-sectional, side view, taken along line A-A of FIG. 2, illustrating a clamp assembly including a unitary clamp bar in accordance with another embodiment of the invention.

As shown in FIGS. 16A-16C, a method of assembling the swivel screw 135 to the clamp bar 130 is shown. In these figures, other components of clamp assembly 100 have been omitted for clarity. In a first step 400 as shown in FIG. 16A, swivel screw 135 and clamp bar 130 are provided and oriented as shown. In a second step 401 as shown in FIG. 16B, swivel screw 135 is advanced toward swivel foot 133 in the direction shown. Left-handed thread portion 138*a* is threadedly engaged with left-handed receiver portion 133*a*, and turned counter-clockwise. In this context and according to convention, right-hand threads run clockwise, and left-hand threads run counterclockwise. Once the swivel screw 135 has been sufficiently advanced, in a third step 402 according to FIG. 16C, the left-handed thread portion 138*a* bypasses left-handed receiver portion 133*a* to form the assembled configuration previously described with respect to FIGS. 8A-8B, and 13-14. Here, the swivel screw 135 becomes fixedly and/or operably coupled to clamp bar 130 via swivel foot 133; when the swivel screw 135 is advanced within clamp assembly 100, a portion of the smooth portion 138*b* of lower portion 138 is configured to advance clamp bar 130 via coupling to swivel foot cavity portion 133*b*; when the swivel screw 135 is retracted, as in the direction shown in FIG. 16C, the right-hand screw of upper screw portion 136 provides the desired translation, and the left-hand thread portion 138*a* of the lower portion 138 ensures proper and operative coupling of clamp bar 130 to the swivel screw 135.

Referring now to FIGS. 17-23D, aspects of the swivel screw 170 and a unitary clamp bar 160 where the lower portion 138 of swivel screw 135 comprises a smooth portion 138*b* forming a substantially spherical profile according to another embodiment of the present invention. The recessed hole 134 as shown in FIG. 8A may be characterized by the arrangement and spacing shown in the cross-sectional view of FIG. 17 (taken along the line A-A of FIG. 2), which illustrates the swivel screw 170 and unitary clamp bar 160 in the context of the clamp assembly 100. Swivel screw 170 according to this embodiment may comprise an upper screw portion 136, a transition portion 137, and a lower portion 138.

Figure 18:
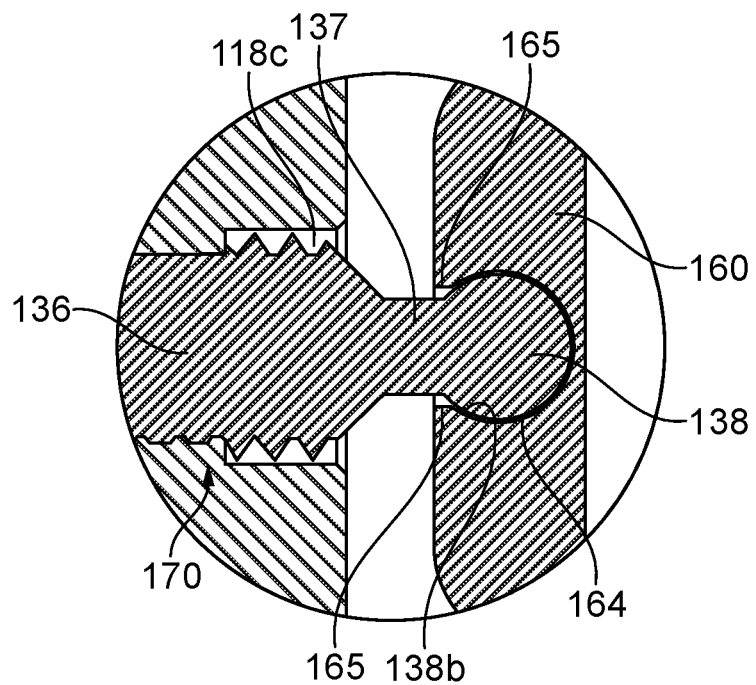
FIG. 18 is an enlarged view in accordance with the line shown in FIG. 17, illustrating a unitary clamp bar in accordance with the invention thereof.
Figure 21:
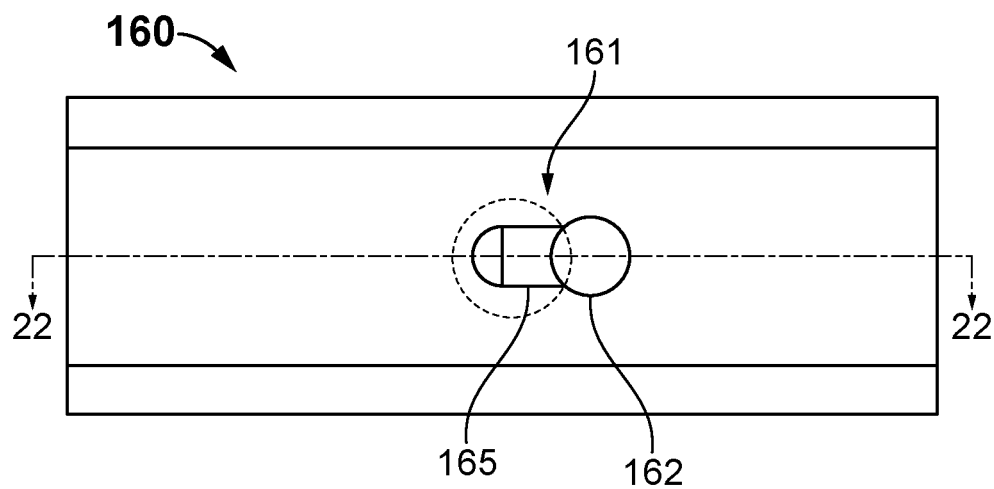
FIG. 21 is a front view of a unitary clamp bar in accordance with the invention thereof.
Figure 22:
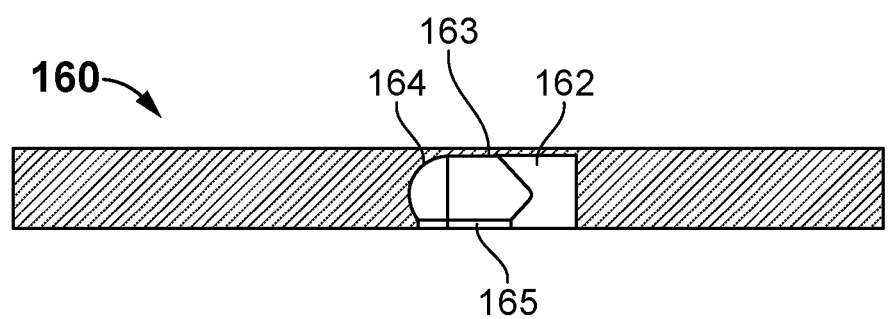
FIG. 22 is a cross-sectional, top view, taken along the line shown in FIG. 21, illustrating a unitary clamp bar of the invention thereof.

As may be seen in the enlarged view of FIG. 18, and in FIGS. 21 and 22, recessed hole 134 of FIG. 8A, may comprise a socket portion 164 and a lip portion 165. The socket portion 164 may be configured to receive the lower portion 138 of swivel screw 170 and the lip portion 165 may be configured to restrict movement of the swivel screw 170 relative to the unitary clamp bar 160, such that in an assembled configuration, a ball-and-socket type joint is formed. Lower portion 138 may comprise a smooth portion 138*b* having a generally spherical profile.

Figure 19:
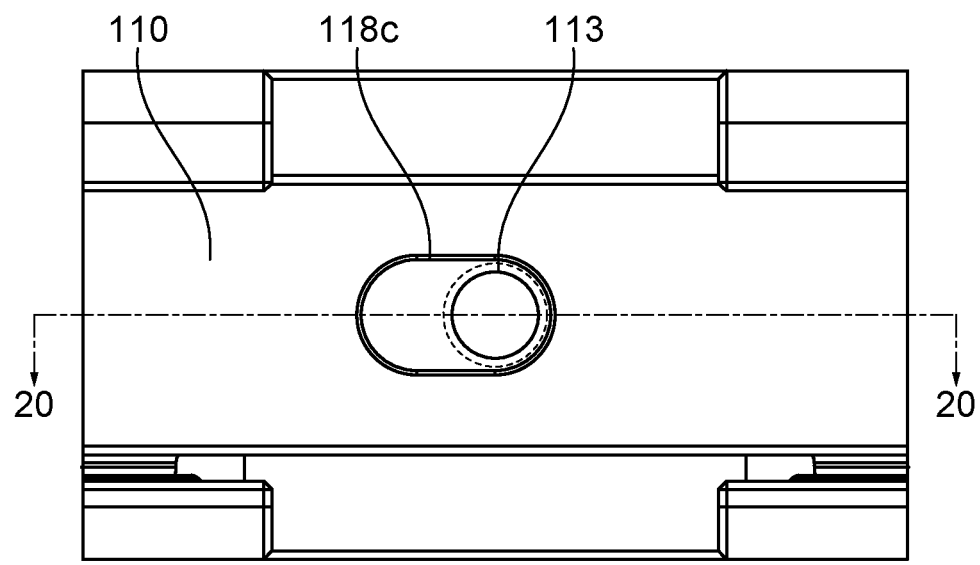
FIG. 19 is a rear view of a clamp body in accordance with the invention thereof.
Figure 20:
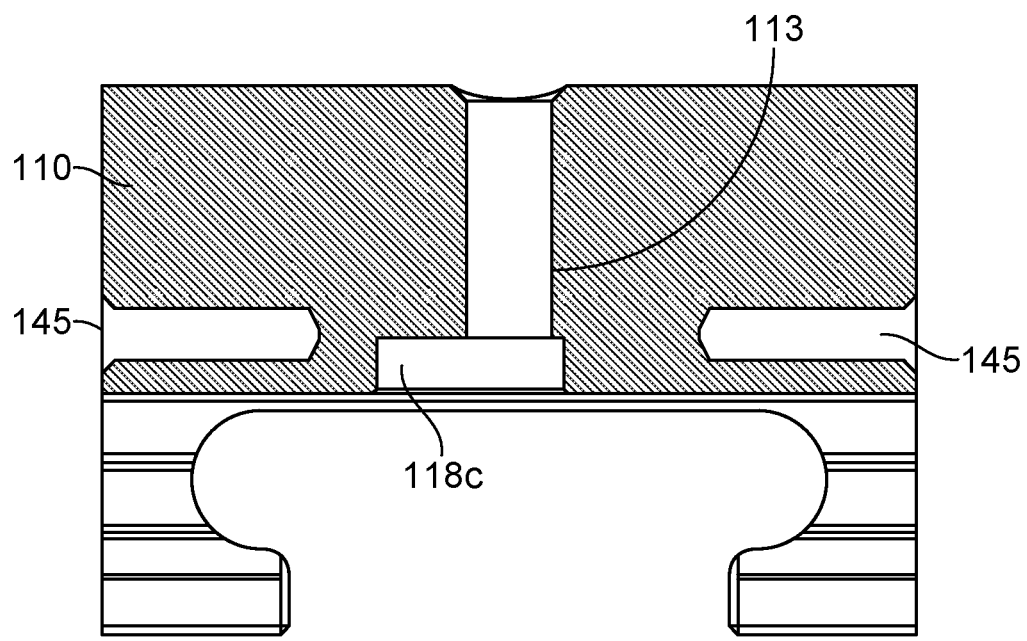
FIG. 20 is a cross-sectional, top view, taken along the line shown in FIG. 19, illustrating a clamp body in accordance with the invention thereof.

Additionally, as shown in FIGS. 19 and 20, body portion 110 may comprise a centrally disposed hole 113 and a third countersink portion 118*c*. According to the cross-sectional view of FIG. 20, taken along the line shown in FIG. 19, third countersink portion 118*c* may form a slotted profile. As shown in FIGS. 21 and 22, unitary clamp bar 160 may comprise a unitary clamp bar recess 161, which may include a receiver portion 162, a socket portion 164, and a slider portion 163 disposed therebetween. According to the cross-sectional view of FIG. 22, taken along the line shown in FIG. 21, the lip portion 165 may extend across the opening formed by the socket portion 164 and at least a portion of slider portion 163.

Figure 23A:
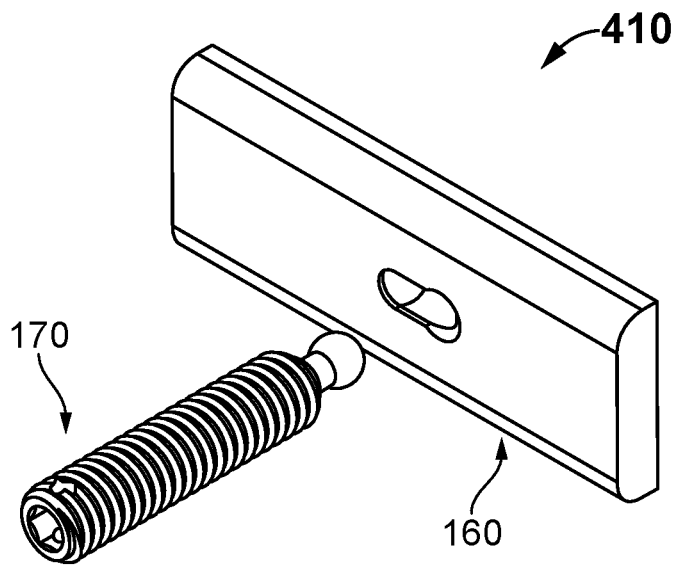
FIGS. 23A-23D illustrate perspective views of a method of assembling a swivel screw and unitary clamp bar in accordance with another embodiment of the invention.
Figure 23B:
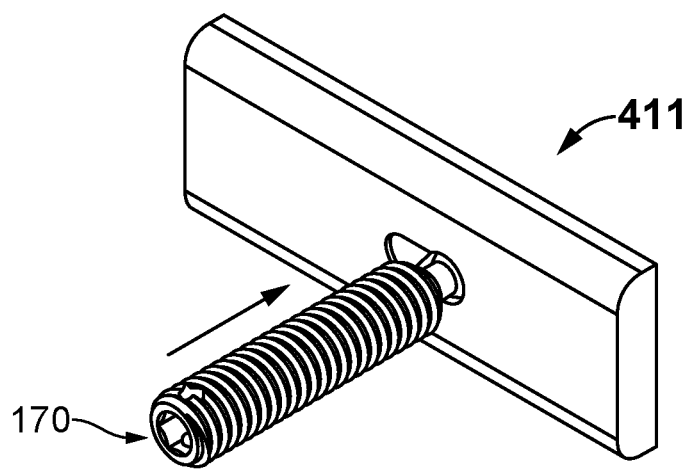
Figure 23C:
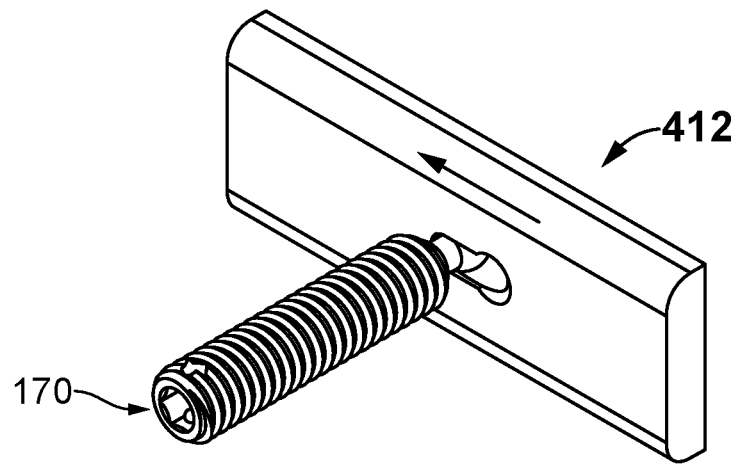
Figure 23D:
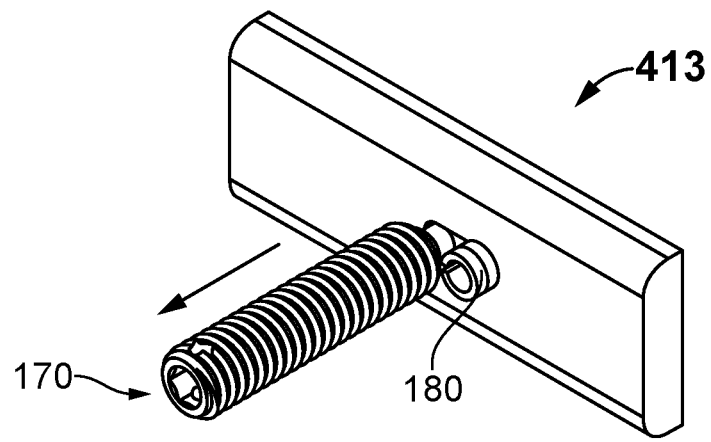

As shown in FIGS. 23A-23D, a method of assembling the swivel screw 170 to the unitary clamp bar 160 is shown. In these figures, other components of clamp assembly 100 have been omitted for clarity. In a first step 410 as shown in FIG. 23A, swivel screw 170 and clamp bar 160 are provided and oriented as shown, wherein the lower portion 138 is aligned and proximate to receiver portion 162. In a second step 411 as shown in FIG. 23B, swivel screw 170 is advanced toward receiver portion 162 in the direction shown, so that lower portion 138 fully enters receiver portion 162. In a third step 412 as shown in FIG. 23C, swivel screw 170 is translated laterally across slider portion 163 to operably couple to socket portion 164. In a fourth step 413 as shown in FIG. 23D, a spring pin 180 may be inserted into receiver portion 162. Spring pin 180 may be characterized by a cylindrical "C" shape, where, upon application of force such as with pliers causes the pin to deform inwardly, and upon removal of said force, the pin resumes the initial shape. Other securing devices may be used and are commonly known in the art. Once spring pin 180 is fixed coupled to the clamp bar 160 in the position shown in FIG. 23D, the swivel screw 170 effectively forms a ball-and-socket type joint, and the swivel screw 170 is substantially prohibited from translating in the direction opposite that described with respect to the lateral direction across slider portion 162 in step 411 of FIG. 23C.

In an assembled configuration, the embodiments described in FIGS. 1-23D concerning the swivel screw 135, 170 and clamp bar 130 and/or unitary clamp bar 180 may be disassembled for sterilization and/or maintenance as desired. Advantageously, the ball-and-socket joint of the instant invention is configured to prohibit buildup of unsterile matter, particularly regarding the embodiment shown and described in FIGS. 17-23D, where in a standard sterilization process, entry of fluid and the like into the recess hole 134 may be admitted so that acceptable levels of sterilization may be obtained. In this way, complete disassembly of the clamp assembly 100 may not be necessary to achieve effective sterilization, thereby saving time and associated costs.

Accordingly, the present invention provides a clamp assembly 100 to secure a strap 106 and/or one or more straps 106 of a patient positioning pad system 108 securely to the side rail 102 of an operating table 104 during a surgical procedure so as to eliminate the patient from shifting on operating table 104 or otherwise changing position on the patient positioning pad 108. The present invention further provides numerous advantages over conventional positioning devices and satisfies patient positioning demands present in new advanced robotic surgical procedures that require holding a patient in a desired position in any angle for a desired surgical procedure, e.g., front-to-back, back-to-front or side-to-side. Moreover, the invention overcomes slippage problems of conventional systems having advantages in providing secure clamping of the strap 106 to the rail 102 of the operating table 104 when the patient is placed in steep Trendelenburg positions that requires re-positioning during surgical procedures, e.g., patient slippage occurs with heavier and larger sized patients being placed in steep Trendelenburg positions.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clamp assembly for securing a strap to a rail of a support table, the clamp assembly comprising:
   a body portion comprising a top portion, a bottom portion, a front portion, a rear portion, and opposing side portions, said body portion further comprising:
      a cavity disposed in between said front and rear portions, said cavity including a cavity surface,
      a strap channel formed in said body portion, centrally along said rear portion, extending from said top portion through to said bottom portion, and formed at a depth that extends to said cavity,
      a rail channel formed in said body portion, centrally along said rear portion, extending from one of said opposing side portions to the other of said opposing side portions, and formed at a depth that extends to said cavity,
      wherein said strap channel and said rail channel form upper rail arms and lower rail arms that extend from said cavity to said rear portion, wherein each of said upper rail arms includes an upper arm surface adapted to rest on an upper edge of the rail and each of said lower rail arms includes a lower rail arm surface adapted to abut a lower edge of the rail, wherein each of said upper rail arms further including a rail flange defining part of said rear portion, and wherein said cavity surface is offset from said rail flanges in the direction of said front portion, said strap channel comprising a strap flange located on each of said upper and lower rail arms, each of said strap flanges extending inwardly from each of said upper and lower rail arms, said strap channel being dimensioned to allow the strap to pass through and extend between said top and bottom portions, and the strap flanges configured to receive the strap within said strap channel;
   a pivot jaw assembly comprising a handle portion, a plurality of jaw rail flange portions, and a plurality of hinge portions, each hinge portion having an opening configured to operably connect to a respective one of said opposing side portions of said body portion using a set screw disposed in each of said openings to form a pivot in each of said opposing side portions of said body portion to allow movement of said pivot jaw assembly about said pivot to rotate said pivot jaw assembly between an opened and a closed position, said pivot jaw assembly configured to rest in a closed position when said clamp assembly is disposed on the rail;
   a swivel screw having an upper screw portion, a lower portion, and a transition portion disposed therebetween, wherein said lower portion is formed substantially spherical and comprises a smooth portion;
   a clamp bar coupled to said lower portion of said swivel screw, said clamp bar configured to move in angular directions with respect to the swivel screw, said clamp bar comprises a unitary clamp bar recess including a socket portion and a lip portion, said socket portion being configured to receive said lower portion such that said lip portion retains said swivel screw about said transition portion, thereby forming a ball-and-socket joint, said clamp bar further comprising a receiver portion and a slider portion, wherein for assembling and/or disassembling said clamp assembly, said receiver portion is configured to receive said lower portion, said slider portion is configured to allow said lower portion to translate laterally towards said socket portion so that said lower portion can be received by said socket portion;
   a knob having an opening adapted to receive said upper screw portion of said swivel screw, said knob adapted to operably move said swivel screw along a centrally-disposed opening in the body portion extending between said front portion and said cavity surface; and
   a spring pin configured to be received by said receiver portion such that, in an assembled configuration, said lower screw portion remains operably coupled to said clamp bar within said socket portion; and
   whereby said clamp bar being adapted to secure the strap against the side rail of the support table when said clamp bar is moved to a second position of said rail channel from a first position adjacent said cavity surface.

2. A clamp assembly for securing a strap to a rail of a support table, the clamp assembly comprising:
   a body portion comprising a top portion, a bottom portion, a front portion, a rear portion, and opposing side portions, said body portion further comprising:
      a cavity disposed in between said front and rear portions, said cavity including a cavity surface,
      a strap channel formed in said body portion, centrally along said rear portion, extending from said top portion through to said bottom portion, and formed at a depth that extends to said cavity,
      a rail channel formed in said body portion, centrally along said rear portion, extending from one of said opposing side portions to the other of said opposing side portions, and formed at a depth that extends to said cavity, wherein said strap channel and said rail channel form upper rail arms and lower rail arms that extend from said cavity to said rear portion, wherein each of said upper rail arms includes an upper arm surface adapted to rest on an upper edge of the rail and each of said lower rail arms includes a lower rail arm surface adapted to abut a lower edge of the rail, wherein each of said upper rail arms further including a rail flange defining part of said rear portion, and wherein said cavity surface is offset from said rail flanges in the direction of said front portion, said strap channel comprising a strap flange located on each of said upper and lower rail arms, each of said strap flanges extending inwardly from each of said upper and lower rail arms, said strap channel being dimensioned to allow the strap to pass through and extend between said top and bottom portions, and the strap flanges configured to receive the strap within said strap channel;

a pivot jaw assembly comprising a handle portion, a plurality of jaw rail flange portions, and a plurality of hinge portions, each hinge portion having an opening configured to operably connect to a respective one of said opposing side portions of said body portion using a set screw disposed in each of said openings to form a pivot in each of said opposing side portions of said body portion to allow movement of said pivot jaw assembly about said pivot to rotate said pivot jaw assembly between an opened and a closed position, said pivot jaw assembly configured to rest in a closed position when said clamp assembly is disposed on the rail;

a swivel screw having an upper screw portion, a lower portion, and a transition portion disposed therebetween, wherein said lower portion is formed substantially spherical and comprises a smooth portion;

a swivel foot fixedly coupled to a clamp bar and including a swivel foot cavity portion defining a swivel foot opening and a thread receiver portion disposed around said swivel foot opening configured to operably couple to a thread portion formed on at least a portion of said lower portion, said thread portion having threads disposed in an opposite winding direction than that of said upper screw portion;

a knob having an opening adapted to receive said upper screw portion of said swivel screw, said knob adapted to operably move said swivel screw along a centrally-disposed opening in the body portion extending between said front portion and said cavity surface; and whereby said clamp bar being adapted to secure the strap against the side rail of the support table when said clamp bar is moved to a second position of said rail channel from a first position adjacent said cavity surface.

3. The clamp assembly of claim 2 wherein, in an assembled configuration, said thread portion advances past said thread receiver portion defined by said swivel foot opening into the cavity portion of the swivel foot, thereby forming a ball-and-socket.

* * * * *